United States Patent [19]
Honkawa et al.

[11] 4,136,959
[45] Jan. 30, 1979

[54] METHOD FOR ANALYZING ONE INGREDIENT OF A THREE INGREDIENT MIXTURE

[75] Inventors: Tadashi Honkawa; Ritsuo Komori, both of Ibaraki, Japan

[73] Assignee: Hitachi, Ltd., Tokyo, Japan

[21] Appl. No.: 763,674

[22] Filed: Jan. 28, 1977

[30] Foreign Application Priority Data

Jan. 28, 1976 [JP] Japan .................................. 51/7471

[51] Int. Cl.² .......................... G01J 3/48; G01J 3/46; G01N 21/06
[52] U.S. Cl. .................................. 356/418; 356/407; 356/436
[58] Field of Search ............... 356/180, 188, 184, 178, 356/199, 201

[56] References Cited
U.S. PATENT DOCUMENTS 3,694,092  9/1972  Hashimoto et al. ................ 356/188
3,994,590  11/1976  DiMartini et al. ................... 356/178

Primary Examiner—Vincent P. McGraw
Assistant Examiner—Rodney B. Bovernick
Attorney, Agent, or Firm—Thomas E. Beall, Jr.

[57] ABSTRACT

A three ingredient mixture is eradiated with light rays of two separate wave lengths selected at which the absorption spectra of at least two of the materials of the mixture intersect. The light rays passing through the materials are detected and separated electrically so that they are processed with coefficients determined from ratios involving the absorption of at least two of the materials, so that the difference in the signals so obtained is quantitatively correlated to only one of the materials in the mixture.

1 Claim, 7 Drawing Figures $\triangle: \Delta D_{540-480} = b\lambda_2 - 9.5 b\lambda_1$ $\times: \Delta D_{560-510} = 2b\lambda_2 - b\lambda_1$

METHOD FOR ANALYZING ONE INGREDIENT OF A THREE INGREDIENT MIXTURE

BACKGROUND OF THE INVENTION

1. Field of the Invention

This invention relates to apparatus suitable for optically and directly analyzing one ingredient in a multi-ingredient mixture.

2. Description of the Prior Art

As apparatus for analyzing one of two ingredients as in a case where two materials A and B are mixed to form a material C, a two-wavelength spectrophotometer has been generally known. In this case, a single sample is irradiated by light rays of two different wavelengths, and the ratio of two signals obtained is taken and is thereafter subjected to the logarithmic conversion. In case of measuring the material to-be-measured A in the coexistent material B, two wavelengths $\lambda_1$ and $\lambda_2$ at which absorbances by the coexistent material B are equal as shown in FIG. 1 must be selected. By way of example, letting the absorbances of the material A at the wavelengths $\lambda_1$ and $\lambda_2$ be $a\lambda_1$ and $a\lambda_2$ and those of the material B be $b\lambda_1$ and $b\lambda_2$, the concentration of the mixture C becomes as follows:

$$c\lambda_1 = a\lambda_1 + b\lambda_1 \quad (1)$$

$$c\lambda_2 = a\lambda_2 + b\lambda_2 \quad (2)$$

On account of the two-wavelength photometry system, a value to be found becomes as follows:

$$\Delta c = c_{\lambda_2} - c_{\lambda_1} = a_{\lambda_2} - a_{\lambda_1} + b_{\lambda_2} - b_{\lambda_1} \quad (3)$$

Here, the two wavelengths $\lambda_1$ and $\lambda_2$ of equal absorbances as to the coexistent material B are selected, so that the following equation holds:

$$b\lambda_2 = b\lambda_1 \quad (4)$$

Therefore, $$\Delta c = a\lambda_2 - a\lambda_1 \quad (5)$$

Accordingly, the influence of the coexistent material is obviated, and one ingredient A can be measured by measuring the mixture C as it is.

With the above method, however, in case where the coexistent material B does not have two wavelengths of equal absorbances as illustrated in FIG. 2, $b\lambda_2 \neq b\lambda_1$, the measurement is impossible. Therefore, the masking of the coexistent material or the pre-treatment of extracting and separating the material to-be-measured is required.

In addition to the foregoing measure, U.S. Pat. No. 3,694,092 has been known. It discloses to the effect that one of mixed ingredients can be simply measured without separation and extraction. Since, however, the two-wavelength photometry system is adopted also in this case, a certain condition is imposed on the selection of the two wavelengths. That is, a wavelength which both the material to-be-measured and the coexistent material absorb must be selected as one of the two wavelengths, and a wavelength which the material to-be-measured does not absorb and which only the coexistent material absorbs must be selected as the other wavelength. Accordingly, although the measurement is possible in case of mixed materials which satisfy the aforecited condition, it becomes impossible in the other case.

SUMMARY OF THE INVENTION

Object of the Invention

An object of this invention is to provide apparatus for analyzing one ingredient in a multi-ingredient mixture as is free from the disadvantages of the prior arts described above.

Another object of this invention is to provide the apparatus in which the concentration of a material to-be-measured can be directly read.

Still another object of this invention is to provide the apparatus which can measure one of mixed ingredients without masking or without the pre-treatment of separation, extraction or the like.

Yet another object of this invention is to provide the apparatus which can measure, not only one of two ingredients, but also one of three ingredients.

Statement of the Invention

In accordance with this invention, there is provided apparatus for analyzing one ingredient in a multi-ingredient mixture that is so constructed that one sample is irradiated by two monochromatic light rays, that respective signals obtained are logarithmically converted independently of each other, that after multiplying the resultant signals by coefficients, the difference between both the signals is obtained, and that if necessary, the difference signal is further multiplied by a coefficient.

The above-mentioned and other features and objects of this invention will become more apparent from the following description taken with reference to the accompanying drawings.

DESCRIPTION OF THE PREFERRED EMBODIMENTS

Figure 1:
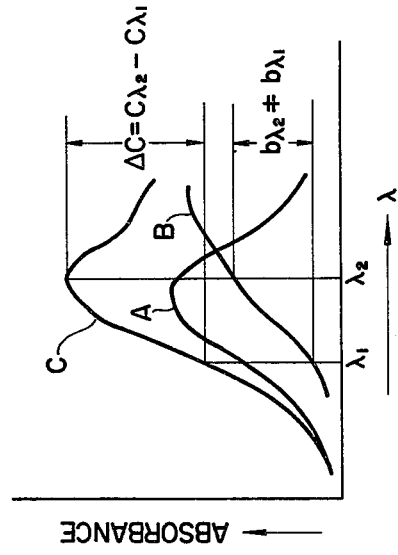
FIG. 1 is a graph for explaining the prior art for measuring one of two ingredients in the case where two wavelengths at which absorbances by a coexistent material become equal are selected.
Figure 2:
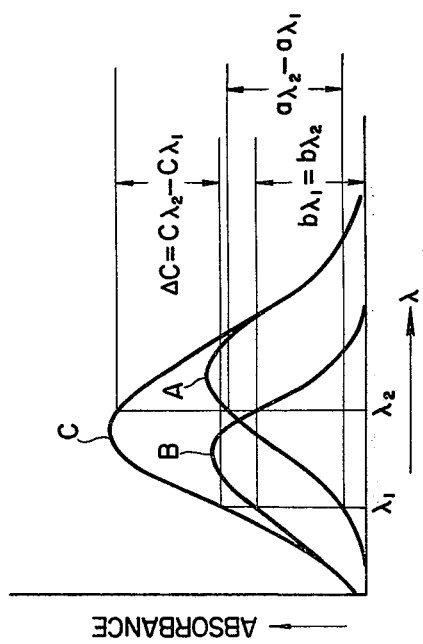
FIG. 2 is a graph for explaining the spectrum absorbing characteristics of the two ingredients in the case where the two wavelengths at which the absorbances by the coexistent material become equal cannot be selected.
Figure 3:
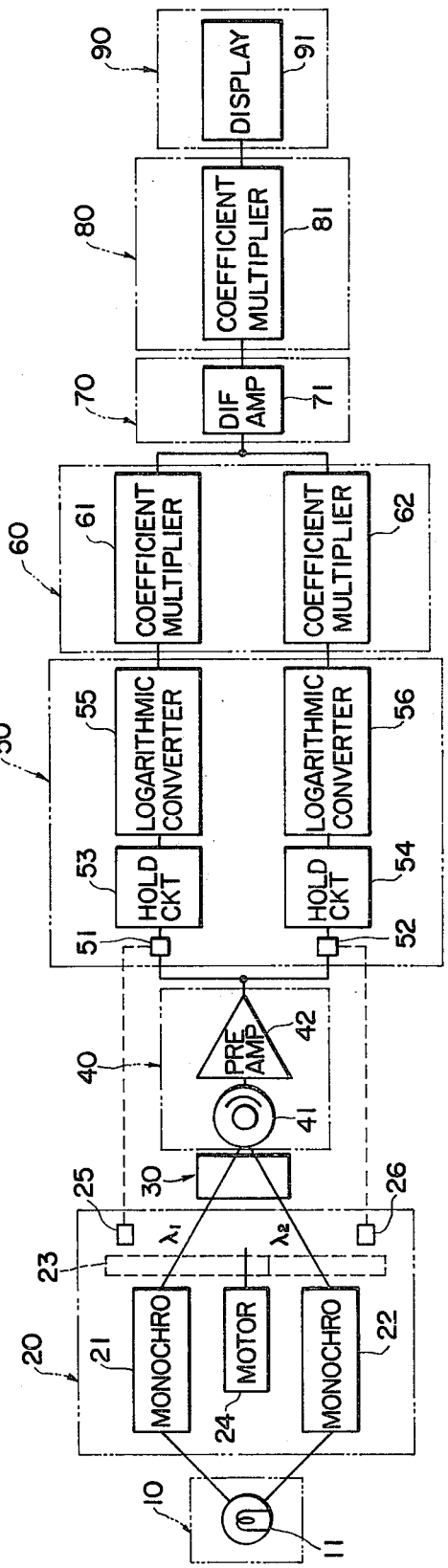
FIG. 3 is a block diagram showing a preferred embodiment of an optical system as well as an electric system employed in the apparatus according to this invention.

FIG. 3 is a block diagram of a preferred embodiment according to this invention, which includes an optical system and an electric circuit. The optical system is composed of a source of light 10 which includes a lamp 11, and wavelength selector 20 which includes first and second monochromators 21 and 22 for monochromating light from the light source 10 and selecting predetermined wavelengths, for example, $\lambda_1$ and $\lambda_2$, chopper 23 for irradiating a sample cell 30 by predetermined monochromatic light rays of, for example, $\lambda_1$ and $\lambda_2$ from the first and second monochromators 21 and 22 by alternately changing-over them in time division, a motor 24 for driving the chopper 23, and detectors 25 and 26 for generating synchronizing signals in synchronism with the rotation of the chopping means 23.

The monochromators can be replaced by monochromatic filters.

The electric circuit is composed of various portions 40–90 to be described below. The portion 40 is a detecting unit which includes a detector 41 for receiving light from the sample cell 30 and converting a light signal into an electric signal, and a pre-amplifier 42 for amplifying the electric signal produced by the conversion in the detector 41. The portion 50 is logarithmic a conversion unit, which includes first and second gate circuits 51 and 52 for carrying out gating operations in synchronism with the rotation of the chopping means 23, first and second hold circuits 53 and 54 for holding first and second electric signals from the respective gate circuits 51 and 52, and logarithmic converters 55 and 56 for logarithmically converting the first and second electric signals held in the respective hold circuits 53 and 54 into third and fourth electric signals. The portion 60 is a coefficient multiplying units, which includes first and second coefficient multipliers 61 and 62 for multiplying by predetermined coefficient values the respective signals produced by the logarithmic conversions in the logarithmic converters 55 and 56. The portion 70 is a difference detecting units, which includes a differential amplifier 71 for evaluating the difference between two signal values obtained by the multiplications by the predetermined coefficient values in the respective coefficient multipliers 61 and 62. The portion 80 is a concentration conversion units, which includes a third coefficient multiplier 81 for further multiplying the difference value obtained in the differential amplifier 71 by a predetermined coefficient for the conversion thereof into a concentration as may be needed. Finally, the portion 90 is a display units which includes a display 91 for indicating an output.

Description will now be made of the operation of the apparatus of the embodiment of this invention constructed as stated above. The light emitted from the source of light 10 is guided to the first and second monochromators 21 and 22, which select the monochromatic light rays of the wavelengths $\lambda_1$ and $\lambda_2$ to be substantially absorbed by the first and second materials, respectively. The light rays of the two wavelengths $\lambda_1$ and $\lambda_2$ are changed-over in time division by the chopper 23, and they alternately permeate through the sample cell 30 containing a sample to-be-measured and get to the detector 41. The light signals alternately detected in the detector 41 are converted into first and second electric signals. Here, the first and second electric signals are proportional to the total transmittances of the light rays of the wavelengths $\lambda_1$ and $\lambda_2$ transmitted through the mixture. The first and second electric signals are led via the pre-amplifier 42 to the first and second hold circuits 53 and 54. In this case, the first and second gate circuits 51 and 52 are rendered operative by synchronizing signals, generated in synchronism with the chopping means 23, so that the first electric signal may be led to the first hold circuit 53 when the light ray of the wavelength $\lambda_1$ has permeated through the sample cell 30 and that the second electric signal may be led to the second hold circuit 54 when the light ray of the wavelength $\lambda_2$ has permeated. After passing through the respective hold circuits 53 and 54, the first and second electric signals are applied to the respective logarithmic converters 55 and 56. In response to the detector 41, the logarithmic converters 55 and 56 logarithmically convert the individual first and second electric signals into the third and fourth electric signals, respectively. Here, the third electric signal is proportional to the total absorbance of the light ray of the first wavelength transmitted through the first and second materials, while the fourth electric signal is proportional to the total absorbance of the light ray of the second wavelength transmitted through the first and second materials.

The third and fourth electric signals are respectively led to the first and second coefficient multipliers 61 and 62. In response to the logarithmic converters 55 and 56, the first and second coefficient multipliers 61 and 62 multiply the third and fourth electric signals by the first and second coefficients and convert them into the fifth and sixth electric signals, respectively. Here, the first and second coefficients are previously determined so that the ratio of the second coefficient to the first coefficient may become equal to the inverse number of the ratio of the absorbance of the light ray of the second wavelength to the absorbance of the light ray of the first wavelength transmitted through only the second material.

The fifth and sixth electric signals are led to the differential amplifier 71. In response to the outputs of the first and second coefficient multipliers 61 and 62, the differential amplifier 71 produces the seventh electric signal representative of the difference between the fifth electric signal and sixth electric signal.

If necessary, the seventh electric signal is led to the third coefficient multiplier 81. In response to the output of the differential amplifier 71, the third coefficient multiplier 81 multiplies the seventh electric signal by the third coefficient. Thus, if necessary, the seventh electric signal is converted into the eighth electric signal indicative of the concentration of the first material.

The seventh electric signal or, if necessary, the eighth electric signal is led to the display means 90, and the concentration, for example, is directly displayed. Accordingly, the output signal $\Delta D$ which is obtained in the apparatus of the embodiment becomes as follows:

$$\Delta D = k_3 \cdot (k_2 \cdot c\lambda_2 - k_1 \cdot c\lambda_1) \tag{6}$$

where $k_1$, $k_2$ and $k_3$ represent the coefficients by which the first, second and third coefficient multipliers 61, 62 and 81 multiply, respectively.

From Eqs. (1) and (2) previously mentioned, Eq. (6) becomes as follows:

$$\begin{aligned}\Delta D &= k_3 \{k_2 (a_{\lambda_2} + b_{\lambda_2}) - k_1 (a_{\lambda_1} + b_{\lambda_1})\} \\ &= k_3 (k_2 a_{\lambda_2} - k_1 a_{\lambda_1} + k_2 b_{\lambda_2} - k_1 b_{\lambda_1})\end{aligned} \tag{7}$$

Here, the coefficients $k_1$ and $k_2$ of the first and second coefficient multipliers 61 and 62 are set so that $\Delta D_B = (k_2 b\lambda_2 - k_1 b\lambda_1)$ to be obtained by measuring the coexistent material B as a simple substance, i.e., the difference of absorbances at the wavelengths $\lambda_1$ and $\lambda_2$ may become zero. In general, it is convenient to adjust the value of lower absorbance to the value of higher absorbance by the coefficient multiplier. This results in setting $k_1$ and/or $k_2$ so as to establish:

$$k_1/k_2 = b\lambda_2/b\lambda_1$$

Thus, $\Delta D$ becomes as follows:

$$\Delta D = k_3 (k_2 a\lambda_2 - k_1 a\lambda_1) \quad (8)$$

As apparent from Eq. (8), by measuring the mixture C, the material to-be-measured A can be directly measured independently of the coexistent material B. Further, by multiplying the output signal of units 50 and 60 by the coefficient of the third coefficient multiplier 81, it is possible to convert the difference absorbance value into the sample concentration value and to directly obtain the sample concentration as the output.

Figure 4:
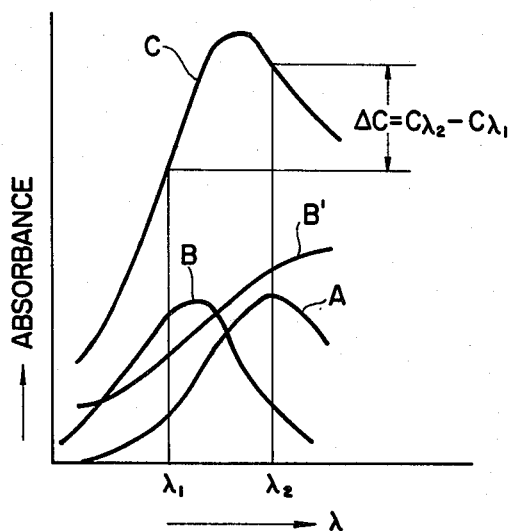
FIG. 4 is a graph for explaining the spectrum absorbing characteristics of a three-ingredient mixture and the respective ingredients thereof as measured by the apparatus shown in FIG. 3.

Description will now be made of a case where, as illustrated in FIG. 4, a coexistent material B' is added and one A of the three ingredients A, B and B' is measured.

$$c\lambda_2 = a\lambda_2 + b\lambda_2 + b'\lambda_2 \quad (9)$$

$$c\lambda_1 = a\lambda_1 + b\lambda_1 + b'\lambda_1 \quad (10)$$

By substituting these equations into Eq. (6), $$D = k_3 (k_2 a\lambda_2 - k_1 a\lambda_1 + k_2 b\lambda_2 - k_1 b\lambda_1 + k_2 b'\lambda_2 - k_1 b'\lambda_1) \quad (11)$$

Here, in order that Eq. (11) may become a value of only the material to-be-measured without being affected by the concentrations of the coexistent materials B and B', the following relations are required:

$$k_1/k_2 = b\lambda_2/b\lambda_1 \, b'\lambda_2/b'\lambda_1 \quad (12)$$

When Eq. (12) holds, Eq. (11) becomes Eq. (13), and only the material to-be-measured A can be measured without the influences of the coexistent materials B and B'.

$$\Delta D = k_3 (k_2 a\lambda_2 - k_1 a\lambda_1) \quad (13)$$

Here, conditions for fulfilling Eq. (12) can be simply found out, in the way to be described below.

(i) First of all, the absorption spectra of the coexistent materials B and B' of arbitrary concentrations alone are sought for, and two wavelengths $\lambda_1$ and $\lambda_2$ are set at two points at which the absorption spectra of the materials B and B' intersect. If the absorption spectra obtained do not have the two intersecting points, the concentration of either the material B or the material B' is arbitrarily varied so as to obtain absorption spectra intersecting at two points. Thus, the relation of $b\lambda_2/b\lambda_1 = b'\lambda_2/b'\lambda_1$ is obtained.

(ii) Secondly, the materials B and B' are set at arbitrary concentrations and are mixed, the wavelengths $\lambda_1$ and $\lambda_2$ are set at the points selected as stated above, and this mixture is measured.

(iii) The coefficient $k_1$ or $k_2$ of the first or second coefficient multiplier 61 or 62 is set so that the absorbances at the wavelengths $\lambda_1$ and $\lambda_2$ may become equal, i.e., the difference $\Delta D$ of the absorbances at $\lambda_1$ and $\lambda_2$ may become zero. In this case, it is convenient that the value of lower absorbance is made equal to the value of higher absorbance by the coefficient multiplier. In this way, the relations of $b\lambda_2/b\lambda_1 = b'\lambda_2/b'\lambda_1 = k_1/k_2$ are obtained.

After the above setting has been done, the mixture C is measured, whereby even when the concentrations of the coexistent materials B and B' change, the material to-be-measured A can be measured without the influences thereof. Further, the output is converted into the concentration by the coefficient $k_3$ of the third coefficient multiplier 81 and can therefore be directly read.

Concrete examples of measurements with the apparatus of the embodiment of this invention will be explained hereunder.

Figure 5:
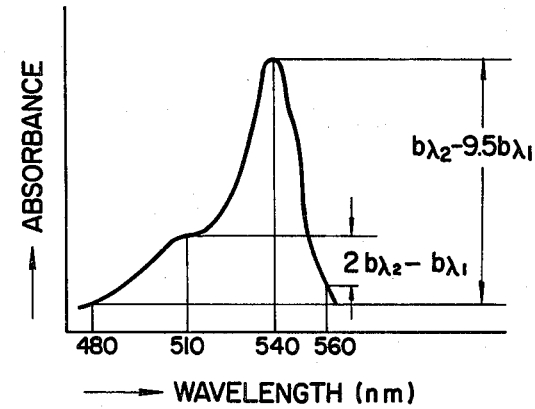
FIG. 5 is a graph for explaining the spectrum absorbing characteristic of the coexistent material alone.
Figure 6:
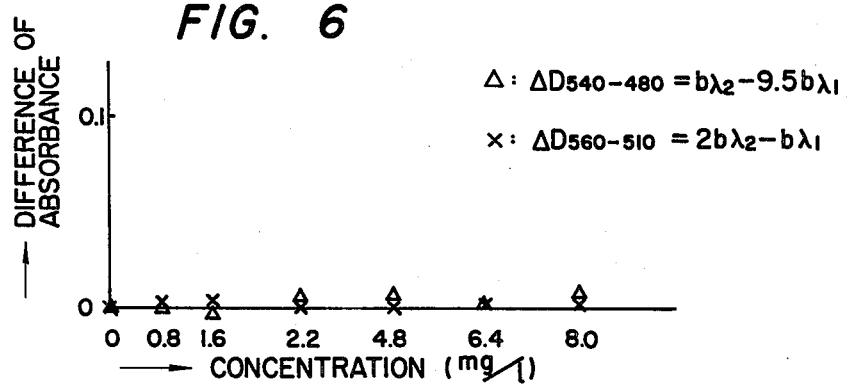
FIG. 6 is a graph showing the results of measurements at the time when the concentration of pholoxine was varied in an example based on this invention.

FIG. 5 is a graph showing the spectrum absorbing characteristic of an edible coloring matter, pholoxine alone. FIG. 6 illustrates the results of measurements in the case of considering the coloring matter, pholoxine as the coexistent material and employing two sorts of combinations of the two wavelengths, i.e., the combination of wavelengths 480 nm and 540 nm and the combination of wavelengths 510 nm and 560 nm. As understood from FIG. 6, when the coefficients $k_1$ and $k_2$ of the first and second coefficient multipliers 61 and 62 are set at $k_1 = 9.5$ and $k_2 = 1$ in the former combination of the wavelengths and at $k_1 = 1$ and $k_2 = 2$ in the latter combination, the difference of absorbances between both the wavelengths becomes null in either case, so that no difference of absorbances arises even by changing the concentrations. In FIG. 6, the axis of abscissas represents the concentration (mg/l), and the axis of ordinates the difference of absorbances $\Delta D$.

Now, Table 1 gives the results of measurements at the time when edible coloring matters, pholoxine and new cocine were mixed and their concentrations were varied. The wavelengths $\lambda_1$ and $\lambda_2$ were set at 540 nm and 480 nm by the wavelength selector 20, respectively. The coefficients $k_1$ and $k_2$ were set at $k_1 = 9.5$ and $k_2 = 1$ in the first and second coefficient multipliers 61 and 62, respectively.

Table 1

| New Cocine (mg/l) | 0 | 5 | 10 | 15 | 20 | 25 |
|---|---|---|---|---|---|---|
| Pholoxine (mg/l) | 8 | 6.4 | 4.8 | 3.2 | 1.6 | 0 |
| Measured Values (mg/l) | 0 | 5 | 9.9 | 14.7 | 19.9 | 25.0 |

As understood from Table 1, notwithstanding that the concentration of the coexistent material, pholoxine varied, the measured values were very close to the concentrations of the material to-be-measured, new cocine.

Figure 7:
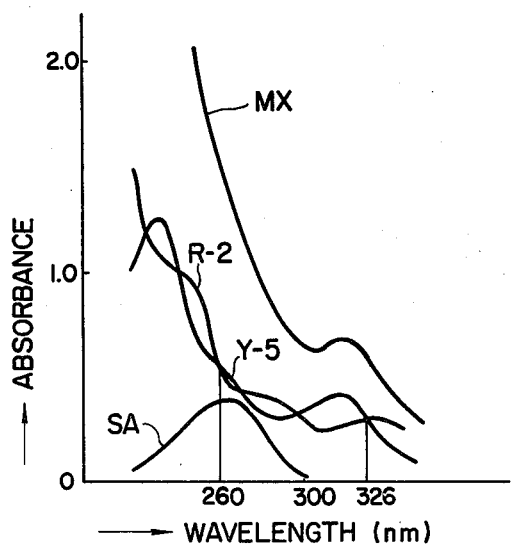
FIG. 7 is a graph for explaining the spectrum absorbing characteristics of amaranth, sunset yellow, sorbic acid and a mixture thereof.

Description will now be made of an example of measurement in the case of a three-ingredient mixture. Referring to FIG. 7, curves R-2, Y-5, SA and MX indicate the spectrum absorbing characteristics of edible coloring matters, amaranth and sunset yellow, sorbic acid, and a mixture thereof, respectively. In measuring the absorbance of sorbic acid in the mixture, amaranth and sunset yellow exist as the coexistent materials. In order to eliminate the influences of the coexistent materials, two wavelengths at which both the absorption spectra intersected, for example, wavelengths 326 nm and 260 nm were selected and set as the wavelengths $\lambda_1$ and $\lambda_2$. The coefficients $k_1$ and $k_2$ of the first and second coefficient multipliers 61 and 62 were set a $k_1 = 1.9$ and $k_2 = 1$. Values obtained under such conditions are given in Table 2 and Table 3.

Table 2

| Amaranth (mg/dl) | 0.2 | 1.0 | 1.5 | 0 | 2 | 0 |
|---|---|---|---|---|---|---|
| Sunset Yellow (mg/dl) | 3 | 2 | 1 | 4 | 0 | 0 |

Table 2-continued

| Measured Values (mg/dl) | 0 | 0 | 0 | 0.001 | 0 | 0 |
| --- | --- | --- | --- | --- | --- | --- |

Table 3

| | | | |
| --- | --- | --- | --- |
| Sorbic acid (mg/dl) | 0.05 | 0.1 | 0.15 |
| Amaranth (mg/dl) | 1.5 | 1.0 | 0.5 |
| Sunset Yellow (mg/dl) | 1.0 | 2.0 | 3.0 |
| Measured Values (mg/dl) | 0.048 | 0.1 | 0.15 |

It will be understood from Table 2 that even when the concentrations of the two coexistent materials vary, the difference of absorbances scarcely occurs. It will also be understood from Table 3 that even when the concentrations of the coexistent materials vary, the measured values are very close to the concentrations of sorbic acid which is the subject of the measurement.

As set forth above, this invention dispenses with the masking of the coexistent material or the pre-treatment such as the extraction and separation of the material to-be-measured as in the prior art. Moreover, two arbitrary wavelengths can be selected, which makes it possible to enjoy the remarkable effect that the concentration of the material to-be-measured can be directly read.

We claim:

1. A method for quantitatively analyzing one ingredient in a mixture of three ingredients comprising the steps of: passing light rays of a first wavelength and a second wavelength through the mixture of the three ingredients, with the first and second wavelengths being selected at which the absorption spectra of at least two of the materials of the mixture intersect; detecting the light waves of the first wavelength transmitted through said mixture and the light rays of the second wavelength transmitted through said mixture and producing first and second electric signals proportional to the transmittance of the first and second wavelengths through the mixture; electrically logrithmically converting the first and second electric signals respectively into third and fourth electrical signals correlated to the absorbance of the light rays of the first wavelength and the light rays of the second wavelength in the mixture; determining one wavelength at which the absorbance of the second and third materials is identical and another separate wavelength at which the absorbance of the second and third materials is identical and measuring the absorbance of the second and third materials at said one and another wavelengths to obtain first and second coefficients having a ratio with respect to each other that is substantially equal to the ratio of the absorbance of the another wavelength in said second material to the absorbance of the one wavelength in said second material, which is substantially equal to the ratio of the absorbance of the another wavelength in said third material to the absorbance of said one wavelength in said third material; and multiplying said third and fourth electric signals by said first and second coefficients, respectively, to obtain fifth and sixth electric signals; differentially amplifying said fifth and sixth electric signals to obtain a seventh differential signal that is quantitatively correlated to only said first material in the mixture.

* * * * *